United States Patent
Browne et al.

(10) Patent No.: US 8,344,176 B2
(45) Date of Patent: Jan. 1, 2013

(54) SYNTHESIS OF SUBSTITUTED HYDROXYMETHYL PHENOLS

(75) Inventors: Roisin Browne, Co. Tipperary (IE); Michael Kilkelly, County Cork (IE)

(73) Assignee: Schwarz Pharma Ltd., County Clare (IE)

( * ) Notice: Subject to any disclaimer, the term of this patent is extended or adjusted under 35 U.S.C. 154(b) by 618 days.

(21) Appl. No.: 12/302,562

(22) PCT Filed: May 26, 2007

(86) PCT No.: PCT/EP2007/004705
§ 371 (c)(1),
(2), (4) Date: May 4, 2009

(87) PCT Pub. No.: WO2007/137799
PCT Pub. Date: Dec. 6, 2007

(65) Prior Publication Data
US 2009/0306421 A1   Dec. 10, 2009

(30) Foreign Application Priority Data

May 31, 2006  (EP) .................................. 06011293
May 31, 2006  (EP) .................................. 06011294
May 31, 2006  (IE) .................................. S2006/0415

(51) Int. Cl.
C07C 67/00  (2006.01)
C07C 211/00  (2006.01)
(52) U.S. Cl. ......................................... 560/250; 564/316
(58) Field of Classification Search .................. None
See application file for complete search history.

(56) References Cited

U.S. PATENT DOCUMENTS 6,713,464 B1  3/2004  Meese et al.
6,858,650 B1  2/2005  Meese

FOREIGN PATENT DOCUMENTS

| CN | 1654452 A | 8/2005 |
| WO | 94/11337 | 5/1994 |
| WO | 99/58478 | 11/1999 |
| WO | 01/35957 | 5/2001 |

OTHER PUBLICATIONS

Carey, et al. "Advanced Organic Chemistry." Springer Media, 2001 (pp. 447-448).
March's Advanced Organic Chemistry, Wilex-Interscience Publication, John Wily & Sons, Inc., 5th edition, 2001 (p. 1214).

*Primary Examiner* — Rosalynd Keys
(74) *Attorney, Agent, or Firm* — Kenyon & Kenyon, LLP

(57) ABSTRACT

The present disclosure relates to a process for the preparation of 2-(3-diisopropylamino-1-phenylpropyl)-4-(hydroxymethyl)phenol or its phenolic monoesters or salts thereof, characterized by the steps of a) reacting a compound of formula (II) with a mixture of a Grignard initiator and Mg in a solvent; b) optionally reducing the temperature of the Grignard reagent to a lower temperature than in step a), and reacting the resulting Grignard reagent with an excess of a carbonate in a solvent, to obtain a compound of formula (III) wherein A is a $C_1$-$C_6$ alkyl, and the further reacting the compound of formula (III) in a known manner to obtain the desired end product.

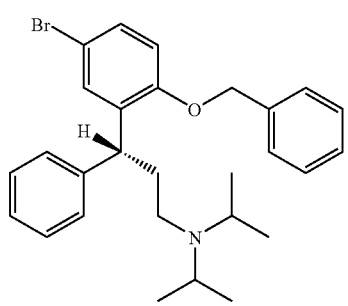

(II)

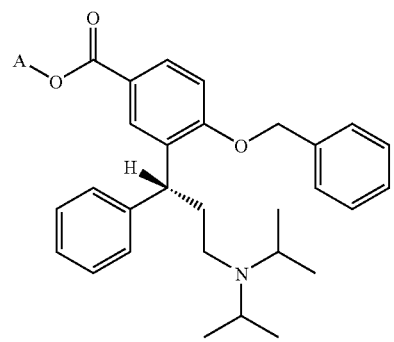

(III)

28 Claims, No Drawings

SYNTHESIS OF SUBSTITUTED HYDROXYMETHYL PHENOLS

CROSS REFERENCE TO RELATED APPLICATION

This application is a 371 of International Patent Application No. PCT/EP2007/004705, filed May 26, 2007, which claims priority to European Patent Application No. 06011294.3, filed May 31, 2006, Irish Patent Application No. S2006/0415, filed May 31, 2006, and European Patent Application No. 06011293.5, filed May 31, 2006. The contents of these applications are hereby incorporated by reference in their entireties.

FIELD

Presently described is a process for the preparation of 2-(3-diisopropylamino-1-phenylpropyl)-4-(hydroxymethyl) phenol which is known as the active metabolite of tolterodine (hereafter referred to as the "Active Metabolite") and its phenolic monoesters by a shortened synthetic route via a Grignard reaction. The target compounds have the following formula (I):

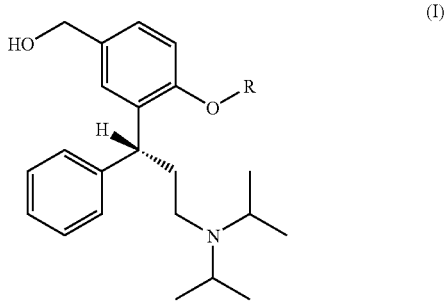

wherein R is hydrogen, a straight or branched $C_1$-$C_6$ alkyl-carbonyl group or a phenylcarbonyl group. If R in formula (I) is hydrogen, the formula represents the Active Metabolite.

A particular preferred example of the phenolic monoesters of formula (I) is Fesoterodine which can be chemically defined as R-(+)-Isobutyric acid 2-(3-diisopropylamino-1-phenylpropyl)-4-(hydroxymethyl)phenol ester. Fesoterodine is represented by formula (Ia) depicted below.

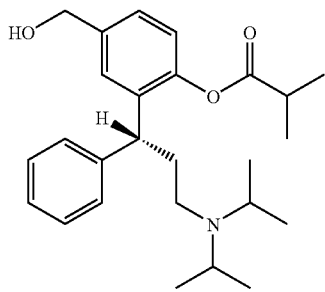

Compounds of formula (I), including the Active Metabolite and its phenolic monoesters of formula (I) are known from WO 99/058478.

Also described herein is a process for the preparation of salts of the compounds of formula (I), specifically including the preparation of salts of Fesoterodine, and more particularly the preparation of the hydrogen fumarate salt of Fesoterodine.

Further disclosed is the preparation of pharmaceutical formulations containing compounds of formula (I), such as Fesoterodine, and the preparation of pharmaceutical formulations containing a pharmaceutically acceptable salt of any of the compounds of formula (I), including, for example, the hydrogen fumarate or hydrochloride hydrate salts of Fesoterodine.

BACKGROUND

In man, normal urinary bladder contractions are mediated, in part, through cholinergic muscarinic receptor stimulation. Muscarinic receptors not only mediate, in part, normal bladder contractions, but also may mediate the main part of the contractions in the overactive bladder resulting in symptoms such as urinary frequency, urgency and urge urinary incontinence.

After administration of Fesoterodine and other phenolic monoesters of formula (I) to mammals, such as humans, these compounds are cleaved by esterases to form the Active Metabolite within the body. The Active Metabolite is known to be a potent and competitive muscarinic receptor antagonist (WO 94/11337). Fesoterodine and other phenolic esters of the formula (I) thus represent potential prodrugs for the Active Metabolite. Fesoterodine, in particular, has been shown to be an effective drug for the treatment of overactive bladder with symptoms of urge urinary incontinence, urgency, and urinary frequency, as well as detrusor hyperactivity (as described in U.S. Pat. No. 6,713,464 and EP-B-1,077,912).

A synthetic approach for the production of the Active Metabolite and monoesters of the phenolic hydroxy group of the Active Metabolite such as Fesoterodine has been described in U.S. Pat. No. 6,713,464 as follows:

In a first step, an ethereal solution is prepared from R-(−)-[3-(2-benzyloxy-5-bromophenyl)-3-phenylpropyl]-diisopropylamine, ethyl bromide and magnesium; this solution is diluted with dry THF and is cooled to −60° C.

In a second step, powdered solid carbon dioxide is added in small portions and the reaction mixture is warmed to room temperature.

In a third step, the reaction is quenched with an aqueous solution of ammonium chloride.

In a fourth step, the aqueous phase of the quenched reaction mixture is adjusted to pH 0.95.

In a fifth step, the pH adjusted phase is filtered and R-(−)-4-benzyloxy-3-(3-diisopropylamino-1-phenylpropyl)-benzoic acid hydrochloride can be recovered from the solid.

In a sixth step, the resulting purified benzoic acid is esterified to its corresponding methyl ester. A diagram summarizing this multi-step synthesis is shown below.

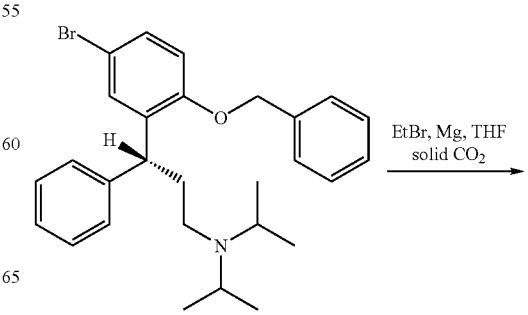

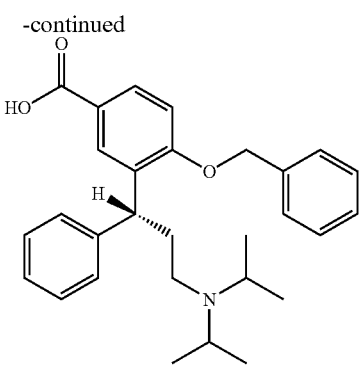

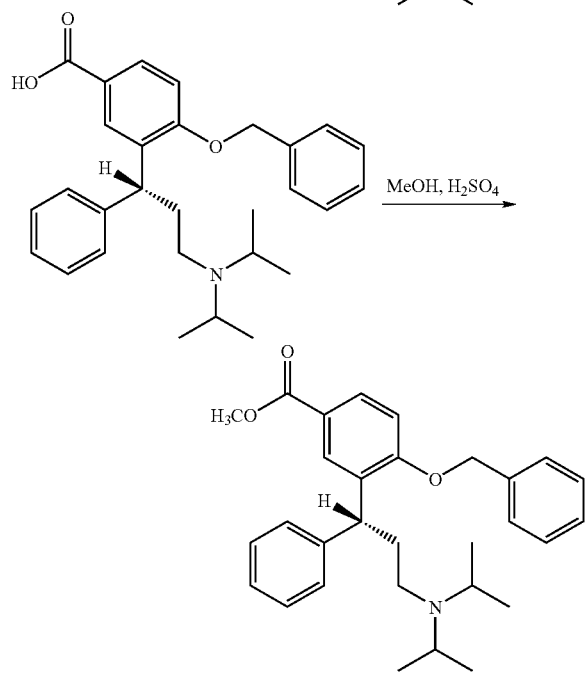

U.S. Pat. No. 6,713,464 further describes converting the methyl ester to the Active Metabolite, and then esterifying the Active Metabolite to a phenolic monoester, such as Fesoterodine.

WO 94/11337 also describes a multi-stage process to synthesize the precursor to the Active Metabolite.

These previously described methods for producing the Active Metabolite require numerous steps that result in complex purification procedures, time-delay, and enhanced possibility of human error, thereby prohibiting optimal efficiency and cost-effectiveness. Also, the solid carbon dioxide used in the art is difficult to handle on large scale due to the need to work at very low temperatures and to add the crushed dry ice portion-wise, and due to the difficulties to control the very exothermic nature of the reaction.

The present disclosure aims to overcome these problems and disadvantages. It has been found that the use of a di($C_1$-$C_6$ alkyl)carbonate, preferably dimethylcarbonate, or the use of a cyclic $C_1$-$C_6$ alkylene carbonate, in the Grignard reaction results in a highly pure product, while at the same time eliminating the production of the benzoic acid and the purification thereof.

The methods disclosed herein are unexpected and are surprising since current and well-known textbooks teach that the addition of Grignard reagents to carbonates and other esters produces tertiary alcohols as a predominant product. For example, in F. A. Carey, R. J. Sundberg, "Advanced Organic Chemistry", Springer Media, 2001, it is taught that the addition of Grignard reagents to esters (including carbonates) is commonly used to produce tertiary alcohols (pages 447-448). Likewise, the well-known compendium "March's Advanced Organic Chemistry", Wilex-Interscience Publication, John Wiley & Sons, Inc., 5$^{th}$ edition, 2001, page 1214, teaches that in Grignard reactions "carbonates give tertiary alcohol in which all three R groups are the same" (page 1214).

Surprisingly, however, in the presently described method the reaction of a carbonate with a Grignard reagent, which is formed after the addition of magnesium and a Grignard initiator to a compound of formula (II), leads to an alkyl ester of formula (III) as the predominate product, while the tertiary alcohol is only formed as a by-product. Typically, between about 60% and about 70% of the direct reaction products of the presently described Grignard reaction is a compound of formula (III).

Also, it turned out, surprisingly, that the tertiary alcohol and other impurities formed during the presently described methods can be easily and very effectively removed during the crystallisation of the ester of formula (III) in isopropanol. This was not predictable from the state of the art.

Accordingly, the use of carbonates, such as dimethylcarbonate or a higher homologue thereof, in the Grignard reaction allows for a shortened and more cost-effective synthetic approach to compounds of formula (I) by eliminating the production of the benzoic acid intermediate and the purification thereof. Moreover, the current methods are better suited for a process on large scale than the reaction requiring solid carbon dioxide that is known from the art.

Moreover, it has been unexpectedly found that the use of methyl magnesium chloride as the Grignard initiator is particularly advantageous. The purity of formula (III) after isopropanol crystallization is typically between about 96.1 and 97.4% when methyl magnesium chloride is used to start the Grignard reaction, whereas the purity of the compound of formula (III) did not exceed about 94% in three batches produced with isopropyl magnesium bromide as the Grignard initiator.

SUMMARY

Described herein is a shortened process for the preparation of compounds of formula (I):

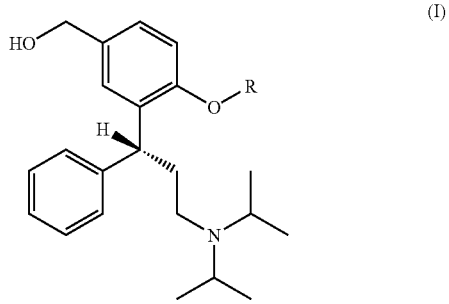

wherein R is hydrogen, a straight or branched $C_1$-$C_6$ alkyl-carbonyl group or a phenylcarbonyl group, including the Active Metabolite and its phenolic monoesters, such as Fesoterodine and its salts, and more particularly the hydrogen fumarate salt of Fesoterodine.

The shortened synthesis of compounds of formula (I) can be characterized by the following steps:
a) reacting a compound of formula (II)

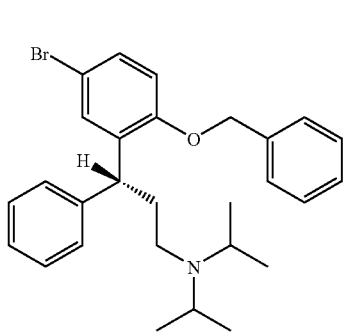

(II)

with a mixture of Mg and a Grignard initiator, preferably in a solvent, to form a Grignard reagent,
b) optionally, reducing the temperature of the Grignard reagent to a lower temperature than in step a) and
c) reacting the Grignard reagent with a carbonate such as a di($C_1$-$C_6$ alkyl)carbonate or a cyclic $C_1$-$C_6$ alkylene carbonate, and preferably with dimethylcarbonate, to obtain a compound of formula (III):

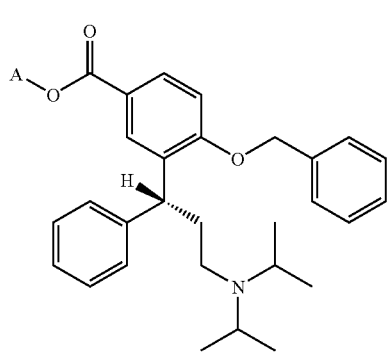

(III)

wherein A is a $C_1$-$C_6$ alkyl, and preferably a methyl group.

In the above disclosed method preferably MeMgCl is being used as the Grignard initiator.

As used in this application, the term "carbonate" includes di($C_1$-$C_6$ alkyl) carbonates, such as for example dimethylcarbonate and diethylcarbonate, as well as cyclic $C_1$-$C_6$ alkylene carbonates such as ethylene carbonate or propylene carbonate.

As used in this application, the term "$C_1$-$C_6$ alkyl" refers to any saturated straight, branched or cyclic hydrocarbon chain having between one and six carbon atoms.

As used in this application, the term "Grignard initiator" refers to a compound of the general formula $R^1$MgX, wherein $R^1$ represents $C_1$-$C_{12}$ alkyl, $C_2$-$C_6$ alkenyl, $C_2$-$C_6$ alkynyl, substituted or unsubstituted phenyl or phenyl($C_1$-$C_6$)alkyl, wherein said phenyl may be substituted, e.g. with ($C_1$-$C_6$) alkyl, ($C_1$-$C_6$)alkoxy or $CF_3$, and wherein X is selected from bromide, chloride and iodide. $R^1$ is preferably selected from $C_1$-$C_6$ alkyl, vinyl, allyl, propenyl, ethynyl, phenyl or benzyl, and is more preferably $C_1$-$C_4$ alkyl. Specific examples of Grignard initiators are isopropyl magnesium bromide, tertiary butyl magnesium chloride or, particularly preferably, methyl magnesium chloride.

Also described herein is a shortened process for the preparation of compounds of formula (I):

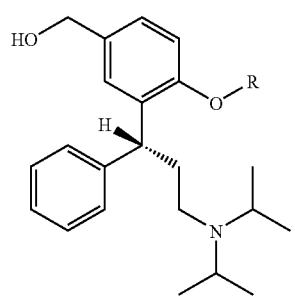

(I)

wherein R is hydrogen, a straight or branched $C_1$-$C_6$ alkyl-carbonyl group or a phenylcarbonyl group, including the Active Metabolite and its phenolic monoesters, such as Fesoterodine and its salts, and more particularly the hydrogen fumarate and hydrochloride hydrate salts of Fesoterodine, wherein said shortened process for the preparation of compounds of formula (I) can be characterized by the following steps:
a) combining a compound of formula (II):

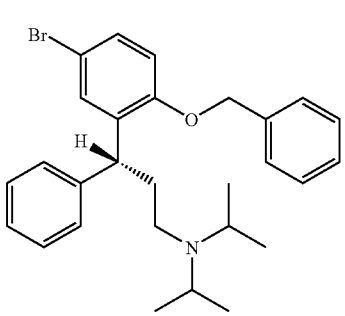

(II)

with Mg and a Grignard initiator, preferably a mixture of Mg and MeMgCl in a solvent, to form a reaction mixture,
b) optionally, reducing the temperature of the reaction mixture of step (a) to a lower temperature than in step (a) and
c) combining the reaction mixture of step (a) with a carbonate, preferably a di($C_1$-$C_6$ alkyl)carbonate or a cyclic $C_1$-$C_6$ alkylene carbonate, and even more preferably with dimethylcarbonate, to obtain a compound of formula (III):

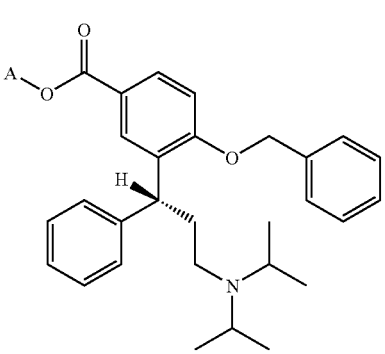

(III)

wherein A is a $C_1$-$C_6$ alkyl, and preferably a methyl group.

Following production, the compound of formula (III) may then be purified, preferably by crystallization in a suitable solvent, preferably in isopropanol.

The resultant compound of formula (III) preferably has a purity of at least about 93%. For example, if isopropyl magnesium bromide is used as the Grignard initiator, a typical purity of the compound of formula (III) after crystallization is between about 93% and about 96%.

More preferably, after the crystallization the compound of formula (III) has a purity of between about 96% and about 99.5%, for example between about 96.1 and about 97.4%. A particular preferred Grignard initiator for a Grignard reaction leading to such a preferred purity is methyl magnesium chloride.

Upon crystallization, the compound of formula (III) may be further reacted in a known manner to obtain a compound of formula (I) or a salt thereof. Most of the remaining impurities, if any, resulting from the Grignard reaction described herein can be further removed during a work-up according to the state of the art (e.g. according to U.S. Pat. No. 6,858,650) to yield the Active Metabolite with a purity of over 99%.

Further described herein are compounds of formula (I) or formula (III), which are made by any of the processes disclosed herein. Even further described are pharmaceutical compositions containing compounds of formula (I) or formula (III), which are made by any of the processes disclosed herein.

Also described herein is a method of producing compounds of formula (III) of at least about 93% purity, and more preferably of at least about 96% to about 99.5% purity, and more specifically of at least about 96.1% to about 97.4% purity, by combining a compound of formula (II):

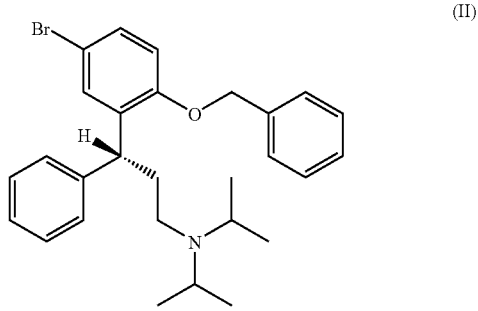

(II)

with Mg and a Grignard initiator, preferably a mixture of Mg and MeMgCl in a solvent, and then preferably reacting the resultant compound with a carbonate as defined further above.

DETAILED DESCRIPTION

The shortened synthesis via a Grignard reaction with a Grignard initiator (preferably MeMgCl), Mg and a carbonate, preferably dimethylcarbonate which can be used in the preparation of the Active Metabolite and its phenolic monoesters of the type disclosed by formula (I), such as Fesoterodine, and more particularly Fesoterodine hydrogen fumarate, is now described in greater detail with reference to preferred embodiments.

In step a) of the process according to the present disclosure, a compound of formula (II)

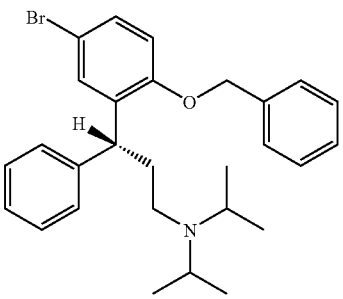

(II)

is reacted with a mixture of Mg and a Grignard initiator in a solvent to form a Grignard reagent.

The molar ratio of the Grignard initiator (e.g. of MeMgCl) to Mg is preferably between about 1:2 and about 2:1, most preferably about 1:1, and the molar ratio of each of the Grignard initiator, and Mg to the compound of formula (II) is preferably between about 1:1 and about 2:1, most preferably about 1:1 to about 1.5:1.

In a particular embodiment, all or part of the Mg may be freshly prepared, for example, by reaction of magnesium chloride with an alkali metal naphthalide, preferably lithium naphthalide (so-called Rieke-Mg).

Preferably, step a) can be carried out by:

a1) dissolving a compound of formula (II) in a suitable solvent to form a solution, and a2) adding said solution to a mixture of MeMgCl and Mg in a suitable solvent to form a Grignard reagent.

A preferred solvent for dissolving compound (II) in reaction step a1) is toluene although other suitable solvents may be used. Preferably the water content in the solution containing compound (II) is not more than about 0.05%.

A preferred solvent for dissolving the Grignard initiator, preferably MeMgCl, in reaction step a2) is preferably THF, however other suitable ethers known to those skilled in the art may be used, including diethylether and tertiary butylmethylether.

The formation of the Grignard reagent as described in step a) is preferably carried out in a temperature range of about 40-55° C. and most preferably in a temperature range of about 40 to about 50° C. The reaction can be conducted under agitation (e.g. stirring) up to completion.

In a preferred embodiment the Grignard then can be cooled down to ambient temperature, e.g. to about 20-25° C. and held, preferably with agitation, for the next steps of the process.

In step c) the resulting Grignard reagent is reacted with a suitable carbonate, such as a di($C_1$-$C_6$ alkyl)carbonate, and preferably with dimethylcarbonate to obtain the compound of formula (III) depicted below wherein A is a $C_1$-$C_6$ alkyl, and preferably a methyl group. An excess of a carbonate, preferably dimethylcarbonate as compared to a compound of formula (II) is preferred, with about 1.1-fold to about 50-fold excess of a carbonate being more preferred, and an about 5 fold to about 50-fold excess being particularly preferable.

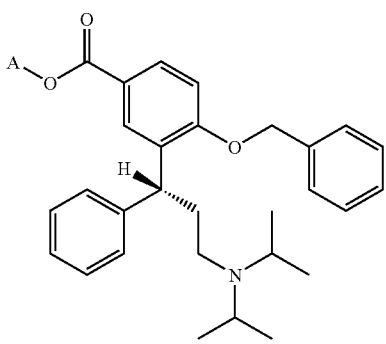

Dimethylcarbonate is the most preferred carbonate.

Other suitable carbonates include di($C_1$-$C_6$ alkyl) carbonates, such as for example diethylcarbonate, and cyclic $C_1$-$C_6$ alkylene carbonates, such as ethylene carbonate or propylene carbonate.

The carbonate may be dissolved in a solvent in step c). A preferred solvent for use in dissolving the carbonate is hexane, however, any inert solvent with a boiling point below the boiling point of the used carbonate, e.g. the preferred dimethylcarbonate, and which is capable of forming an azeotrop with water, including heptane, hexane-isomers and suitable mixtures thereof, can be used.

A part of the hexane used to dissolve the carbonate, preferably dimethylcarbonate, may be removed by distillation, such as azeotropic distillation, before the Grignard reagent is added. This distillation can remove up to about 90 to about 95% of the hexane. The solvent distillation also removes water from the carbonate solvent mixture, which can minimize the formation of a des-bromo amine impurity when combined with the Grignard reagent. Preferably, the water content of the distilled carbonate solvent mixture should be no more than about 0.1 wt %, and more preferably no more than about 0.05 wt %, even more preferably no more than about 0.01 wt %.

In the most preferred embodiment of the present invention, the reaction of the Grignard reagent with carbonate, preferably with dimethylcarbonate, is carried out at a temperature below about 10° C., under agitated conditions.

One preferred option is to add the Grignard reagent (e.g. the MeMgCl) slowly to the stirring carbonate solvent mixture to allow for a rapid and homogenous dilution of the formed ester of formula (III) in the reaction solution. The agitation speed during the addition and subsequent reaction of the Grignard reagent with the carbonate is preferably as high as possible, e.g. at least about 75 rpm and preferably at least about 90 rpm.

Another option is to add the carbonate solvent mixture to the Grignard reagent, preferably under stirring. The preferred stirring time is about 2-3 hrs.

Step c) is completed by quenching the reaction mixture with a suitable reagent. A preferred quenching reagent is aqueous ammonium chloride, although other quenching agents known to those skilled in the art may be used, including aqueous ethylacetate, aqueous sodium chloride or aqueous hydrochloric acid solution.

Subsequently a solvent exchange from the Grignard solvent (e.g. toluene and/or THF) to a solvent suitable for the crystallisation (e.g. isopropanol) is performed.

Isopropanol has been found to be a very effective solvent for the purification of R-(-)-4-Benzyloxy-3-(3-diisopropylamino-1-phenylpropyl)-benzoic methylester.

One preferred embodiment of the present invention is therefore the crystallisation of a compound of formula (III), and preferably of R-(-)-4-Benzyloxy-3-(3-diisopropylamino-1-phenylpropyl)-benzoic methylester in isopropanol.

Another preferred embodiment is a process for the preparation of a compound of formula (I) as described further above, or a salt thereof, characterized in that said process comprises the step of crystallizing a compound of formula (III), and preferably of R-(-)-4-Benzyloxy-3-(3-diisopropylamino-1-phenylpropyl)-benzoic methylester, in isopropanol.

Suitable workup steps after the addition of the quenching reagent are e.g.
- washing with water;
- removal of water from organic phase e.g. by azebtropic drying;
- removal of organic phase by distillation;
- crystallisation in isopropanol; and
- optionally washing in a suitable solvent such as isopropyl alcohol and drying.

Thereafter a compound of formula (III) can be isolated in good purity (usually between about 96% and about 99.5%) and yield.

The process described above is disclosed in more detail in Example 1 of the experimental part of this application.

Another preferred embodiment of the present invention is a method for the preparation of a compound of formula (I)

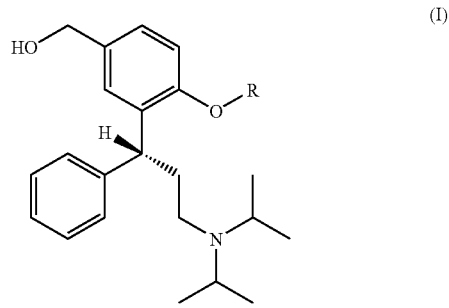

wherein R is hydrogen, a straight or branched $C_1$-$C_6$ alkylcarbonyl group or a phenylcarbonyl group, or a salt thereof, or a precursor to a compound of formula (I), comprising the step of crystallizing a compound of formula (III) as defined further above, and preferably of R-(-)-4-Benzyloxy-3-(3-diisopropylamino-1-phenylpropyl)-benzoic methylester in isopropanol.

The compound of formula (III) can then be further reacted to obtain a compound of formula (I).

A particularly preferred embodiment of the present invention is a process for the preparation of the Active Metabolite, and, if desired, its phenolic monoesters including particularly Fesoterodine or a salt thereof, preferably a pharmaceutically acceptable salt of Fesoterodine, and most preferably the hydrogen fumarate salt of Fesoterodine, which process includes the steps of:

a1) dissolving the compound of formula (II) in a solvent, such as toluene, to form a reaction mixture, a2) adding said reaction mixture to a mixture of the Grignard initiator, preferably MeMgCl, Mg and THF to form a Grignard reagent, wherein the reaction can be performed at a reaction temperature of about 40° C. to about 50° C., b) optionally reducing the temperature of the Grignard reagent to a temperature below the temperature of step a2), and more preferably in the range of about 20 to about 25° C.

and maintaining the Grignard reagent at the lower temperature, optionally under agitation, and c) reacting the resulting Grignard reagent with an excess of carbonate, preferably dimethylcarbonate, in hexane, at a reaction temperature of below about 10° C. and at an agitation speed of at least about 90 rpm, followed by quenching the thus obtained mixture with an aqueous ammonium chloride solution to obtain a compound of formula (III). This compound can then be isolated and purified as described above.

After formation of the compound of formula (III), one option is to further react the compound of formula (III) to obtain a compound of formula (I). This can be accomplished, for example, as follows:

d) reducing the methylester to the corresponding methylalcohol, and

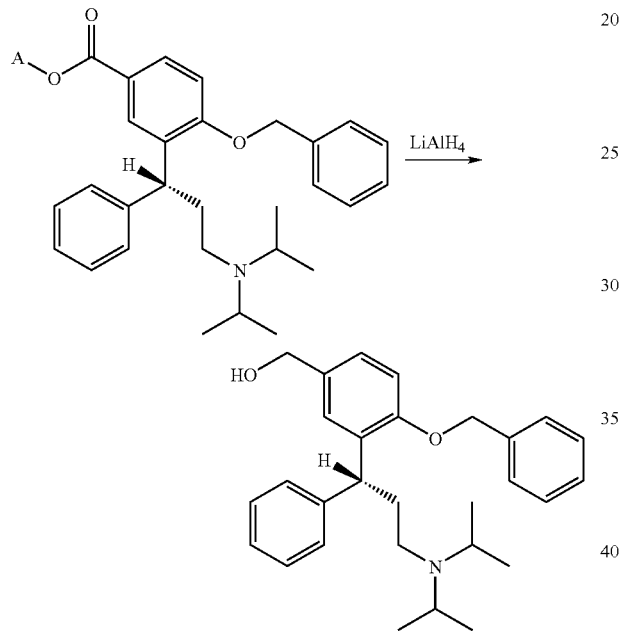

e) debenzylating the protected alcohol to form the Active Metabolite mentioned above.

Another option is to convert the Active Metabolite to an ester thereof such as Fesoterodine or a salt of Fesoterodine, preferably the hydrogen fumarate salt of Fesoterodine, by:

f) phenolic monoacylation, and g) salt formation

Examples of steps d) to g) are disclosed e.g. in U.S. Pat. No. 6,858,650, which is incorporated herein by reference.

The formation of other phenolic monoesters of the Active Metabolite is possible by using other organic acid halides in step f) of the above scheme.

The final compound (I) or (Ia) (phenolic monoesters of the Active Metabolite including Fesoterodine or pharmaceutically acceptable salts thereof) can then be formulated in a known manner to obtain an oral, parenteral, or transdermal medicament.

Another aspect of the present invention is a process for the preparation of a precursor to the compounds of formula (I) including the Active Metabolite or Fesoterodine, comprising the step of reacting carbonates, such as dimethylcarbonate, with a Grignard reagent to obtain a compound of formula (III)

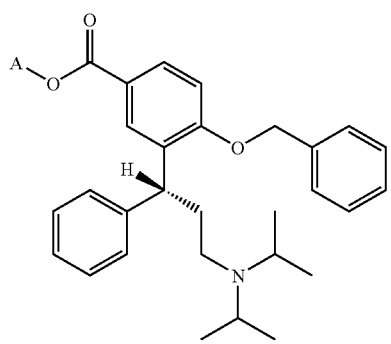

wherein A is a $C_1$-$C_6$ alkyl group, and
wherein the Grignard reagent is formed by reacting a compound of formula (II)

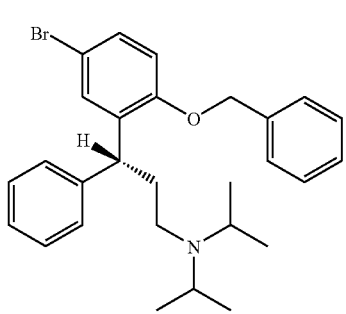

with a mixture of the Grignard initiator, preferably MeMgCl, and Mg in a solvent. In this method the compound of formula (III) can be suitably worked up by the crystallisation in isopropanol, as described further above.

The present disclosure is further illustrated by the following non-exhaustive examples. The examples do not intend to limit the scope of this disclosure as defined in the claims below. The starting compound of formula (II) can be prepared in a known manner, e.g. such as described in the Experimental Part of U.S. Pat. No. 6,713,464.

Further preferred embodiments of the present invention are:

A) A process for the preparation of a compound of formula (I)

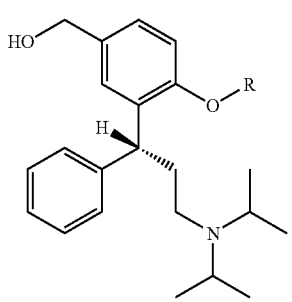

wherein R is hydrogen, a straight or branched $C_1$-$C_6$ alkylcarbonyl group or a phenylcarbonyl group,
or a salt thereof, characterized by the steps of
a) reacting a compound of formula (II)

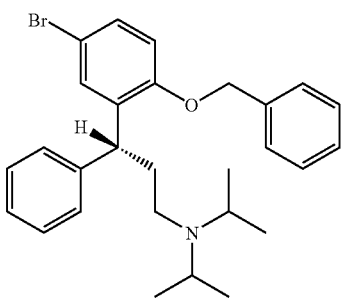

with a mixture of MeMgCl and Mg in a solvent to form a Grignard reagent,
b) optionally reducing the temperature of the Grignard reagent to a temperature below the temperature of step a), and
c) reacting the Grignard reagent with an excess of dimethylcarbonate to obtain a compound of formula (III)

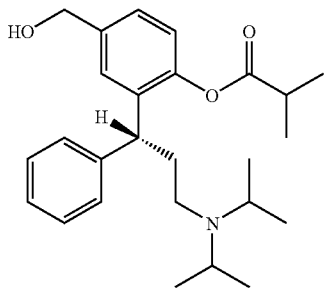

wherein A is a methyl group, and then further reacting the compound of formula (III) in a known manner to obtain a compound of formula (I) and optionally salt formation.

B) The process according to embodiment A), wherein the compound of formula (III) is crystallised prior to its reaction to formula (I).

C) The process according to embodiment B), wherein the crystallisation of the compound of formula (III) is performed in isopropanol.

D) The process according to any of the embodiments A)-C), wherein the compound of formula (I) is Fesoterodine having the formula (Ia)

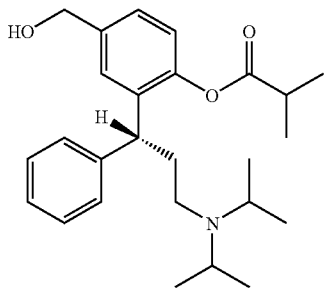

or a salt thereof.

E) The process according to embodiment D) wherein the salt of Fesoterodine is the hydrogen fumarate.
F) The process according to any one of embodiments A)-E) characterized in that in step c) dimethylcarbonate is used in about 5-fold to 50-fold excess.
G) The process according to any one of the embodiments A)-F) characterized in that in step c) a solvent is used, preferably hexane.
H) The process according to embodiment G) characterized in that in step c) the dimethylcarbonate is dissolved in hexane and then distilled to reduce the water content to 0.01% or below and then the Grignard reagent is added.
I) The process according to any one of embodiments A)-H) wherein the reaction step c) is followed by quenching the mixture with a suitable reagent.
J) The process according to embodiment I), wherein the reagent is aqueous $NH_4Cl$.
K) The process according to any one of the embodiments A)-J), wherein the molar ratio of MeMgCl to Mg is between 1:2 and 2:1, and the molar ratio of MeMgCl to the compound of formula (II) is between about 1:1 and 2:1.
L) The process according to any one of the embodiments A)-K) characterized in that step a) is conducted by
  a1) dissolving the compound of formula (II) in a suitable solvent to form a solution, and
  a2) adding said solution to a mixture of MeMgCl and Mg in a suitable solvent.
M) The process according to embodiment L) wherein the solvent in step a1) used for dissolving the compound of formula (II) is toluene.
N) The process according to any of embodiments L) or M) characterized in that the solvent in step a2) is THF.
O) The process according to any of embodiments L) to N) wherein
  in step a1) the compound of formula (II) is dissolved in toluene,
  in step a2) said solution is added to a mixture of MeMgCl and Mg in THF and stirred up to the completion of the reaction,
  in step b) the mixture as obtained in step a2) is maintained under stirring,
  in step c) the mixture is added to an excess of dimethylcarbonate in hexane, followed by quenching with aqueous $NH_4Cl$.
P) The process according to any one of embodiments A) to O) characterized in that the reaction temperature of step a) is between 40 and 50° C.
Q) The process according to any one of embodiments A) to P) characterized in that the reaction temperature of step b) is between 20 and 25° C.
R) The process according to any one of embodiments A) to Q) characterized in that the reaction temperature of step c) is below 10° C.
S) The process according to any one of embodiments A) to R) characterized in that in step c) the reaction mixture is stirred at an agitation speed of ≧90 rpm.
T) A process for the preparation of a pharmaceutical composition containing Fesoterodine hydrogen fumarate comprising the steps of
  (i) preparing Fesoterodine hydrogen fumarate by a process according to any of the preceding embodiments, and
  (ii) formulating the thus obtained Fesoterodine hydrogen fumarate in a known manner to obtain a pharmaceutical composition.
U) A process for the preparation of a precursor to or intermediate of the production of the Active Metabolite or to Fesoterodine comprising the step of reacting dimethylcarbonate with a Grignard reagent to obtain a compound of formula (III)

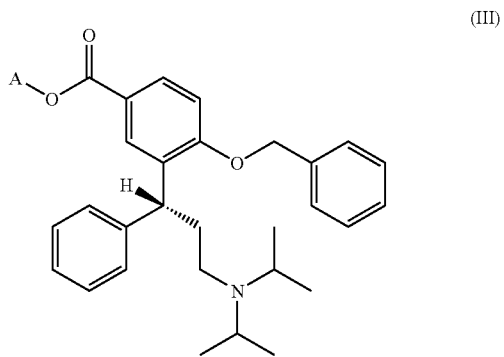

wherein A is a methyl group, and
wherein the Grignard reagent is formed by reacting a compound of formula (II)

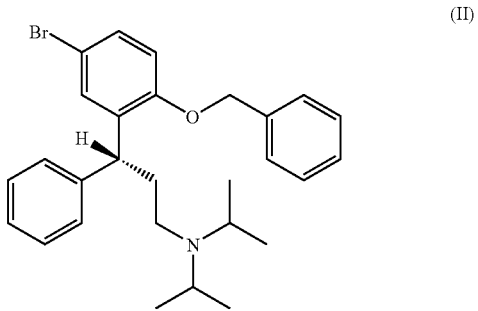

with a mixture of MeMgCl and Mg in a solvent.
V) Method according to embodiment U) comprising the crystallisation of the compound of formula (III) in isopropanol.

EXAMPLES

Example 1

Preparation of R-(−)-4-Benzyloxy-3-(3-diisopropylamino-1-phenylpropyl)-benzoic methylester of formula (III)

(a) Stoichiometry MeMgCl:Mg: R-(−)-[3-(2-Benzyloxy-5-bromophenyl)-3-phenylpropyl]-diisopropylamine=1.5:1.5:1.0

A mixture of magnesium (18 kg, 741 mol) and THF (1066 kg) was charged in a suitable vessel, followed by the addition of methylmagnesium chloride (3M in THF, 246 kg, 743 mol). The solution of R-(−)-[3-(2-Benzyloxy-5-bromophenyl)-3-phenylpropyl]-diisopropylamine (formula (II)), prepared from 486 mol R-(−)-3-(2-Benzyloxy-5-bromophenyl)-3-phenylpropionic acid by the procedure described in U.S. Pat. No. 6,713,464), was then added, while maintaining a reaction temperature of about 40° C. to about 50° C. Upon reaction completion the Grignard reagent of R-(−)-[3-(2-Benzyloxy-5-bromophenyl)-3-phenylpropyl]-diisopropylamine (formula (II)) was maintained at temperature of about 20° C. to about 25° C. In a glass lined vessel, an excess of dimethylcarbonate (1312 kg, 14 kmol) in hexane (1846 kg) was distilled at atmospheric pressure to a set volume range of 1200-1260 L and analysed for water content until a water content of equal to or less than 0.01% (by weight) was reached. The Grignard reagent was then charged to the dimethyl carbonate solution, via a filter in order to remove any residual magnesium, while maintaining the temperature below 10° C. The agitation speed during this addition and subsequent reaction was ≧90 rpm.

The mixture of the Grignard reagent and carbonate-solvent was quenched with aqueous ammonium chloride (660 kg) in a stainless steel vessel. After agitation the biphasic mixture was allowed to settle and the layers were separated. Optionally, an excess of water can be added prior to the phase separation to dissolve Mg salts that can precipitate during the ammonium hydrogen chloride quench. After the additional charge of water the layers can be separated, the aqueous layer extracted with toluene and the organic phases combined. The organic layer was washed twice with water (2×600 kg).

The organic phase was distilled to a volume range between about 1400-1750 L in a stainless steel vessel, and was then transferred to a glass lined vessel before a solvent exchange was performed with a charge of isopropanol and distillation repeated. If required, an additional isopropanol solvent exchange can be performed. Upon removal of excess dimethylcarbonate and toluene, the organic solution was reduced to a volume range of 400 to 800 L.

The mixture was then aged at about 20° C. to about 25° C. until precipitation had occurred, then cooled and aged further at about 0° C. to about 5° C. for a minimum of about 2 hours. The mixture was then centrifuged to separate the precipitate, which was then washed with chilled isopropanol (63 kg). The resulting R-(−)-4-Benzyloxy-3-(3-diisopropylamino-1-phenylpropyl)-benzoic methylester (formula (III)) was dried at about 40° C. to about 50° C. and was obtained in crystalline form.

Six batches of R-(−)-4-Benzyloxy-3-(3-diisopropylamino-1-phenylpropyl)-benzoic methylester prepared with the following representative purities were:
Batch 1: 96.5%
Batch 2: 97.4%
Batch 3: 96.9%
Batch 4: 96.4%
Batch 5: 96.4%
Batch 5: 96.9%
Batch 6: 96.1%

(b) Stoichiometry MeMgCl:Mg: R-(−)-[3-(2-Benzyloxy-5-bromophenyl)-3-phenylpropyl]-diisopropylamine=1:1:1

The Grignard was performed as described in (a), with the only difference that the stoichiometry changed as indicated above.

As the result R-(−)-4-Benzyloxy-3-(3-diisopropylamino-1-phenylpropyl)-benzoic methylester was obtained in a purity of 99.4%.

Example 2

Preparation of R-(+)-[4-Benzyloxy-3-(3-diisopropylamino-1-phenylpropyl)-phenyl]-methanol (Reduction)

A solution of R-(−)-4-Benzyloxy-3-(3-diisopropylamino-1-phenylpropyl)-benzoic methylester (28 g) was dissolved in dry diethyl ether (230 mL). This solution was slowly (about 2 h) dropped under a nitrogen atmosphere to a suspension of lithium aluminium hydride (1.8 g) in ether (140 mL) at a temperature below about 20° C. After stirring for about 18 hrs, the reaction was quenched by the addition of water (4.7 mL). The organic phase was dried over anhydrous sodium sulphate, filtered and evaporated to dryness to provide R-(+)-[4-Benzyloxy-3-(3-diisopropylamino-1-phenylpropyl)-phenyl]-methanol (26 g, 98.9% yield) as an oil which gradually crystallized.

Example 3

Preparation of R-(+)-2-(3-Diisopropylamino-1-phenylpropyl)-4-hydroxymethylphenol (Debenzylation)

A solution of R-(+)-[4-Benzyloxy-3-(3-diisopropylamino-1-phenylpropyl)-phenyl]-methanol (9.1 g) in methanol (100 mL) was hydrogenated over Raneynickel (4.5 g) under ambient conditions. After complete hydrogenolysis, as determined by thin layer chromatography taken at about 4-5 hours, the catalyst was filtered off and the solution was evaporated to dryness to leave an oil (6.95 g, 96.5% yield) which was then dissolved in ethyl acetate. This solution was then washed with an aqueous sodium hydrogen carbonate solution (5 wt %). The organic phase was separated and dried by azeotropic distillation in ethyl acetate. The ethyl acetate solution was then further distilled to a volume in which 1 part (by weight) of R-(+)-2-(3-diisopropylamino-1-phenylpropyl)-4-hydroxymethylphenol was dissolved in 1.5 part (by volume) of ethylacetate. This solution was then cooled down to about −10° C. and was stirred for about 30-60 min. R-(+)-2-(3-diisopropylamino-1-phenylpropyl)-4-hydroxymethylphenol can then be isolated as the precipitate and can be further washed with a small volume of cold ethyl actetate.

The invention claimed is:

1. A process for the preparation of a compound of formula (I)

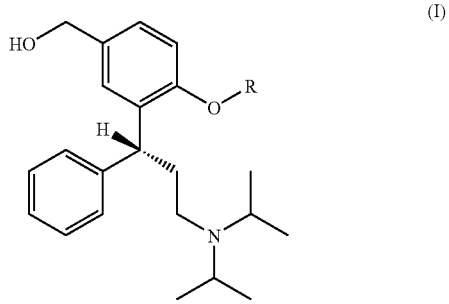

wherein R is hydrogen, a straight or branched $C_1$-$C_6$ alkylcarbonyl group or a phenylcarbonyl group,
or a salt thereof, characterized by the steps of
a) reacting a compound of formula (II)

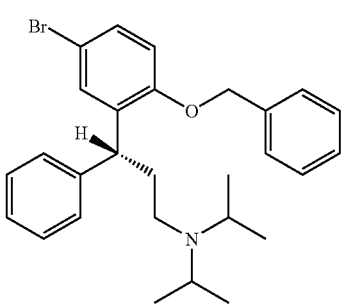
(II)

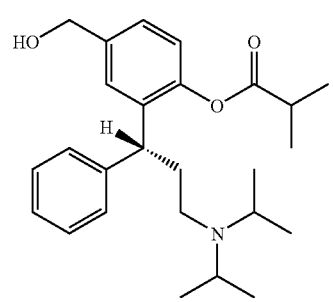
(Ia)

with a mixture of Mg and a Grignard initiator of the formula R1MgX, wherein R1 represents $C_1$-$C_{12}$ alkyl, $C_2$-$C_6$ alkenyl, $C_2$-$C_6$ alkynyl, substituted or unsubstituted phenyl or phenyl($C_1$-$C_6$)alkyl, and wherein X is selected from bromide, chloride and iodide to form a Grignard reagent, and c) reacting the Grignard reagent with an excess of a carbonate selected from the group of di($C_1$-$C_6$ alkyl) carbonates and cyclic $C_1$-$C_6$ alkylene carbonates to obtain a compound of formula (III)

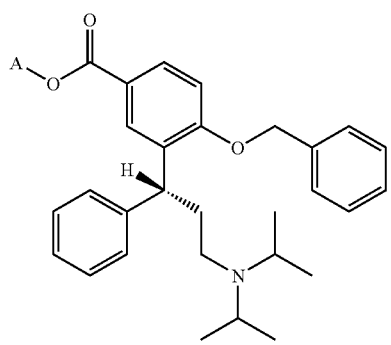
(III)

wherein A is a $C_1$-$C_6$ alkyl group, and then further reacting the compound of formula (III) to obtain a compound of formula (I).

2. The process of claim 1 which further comprises step b), reducing the temperature of the Grignard reagent to a temperature below the temperature of step a), where step b) is carried out before step c).

3. The process of claim 1, wherein the obtained compound of formula (I) is converted into a salt.

4. The process according to claim 1, wherein the Grignard initiator is methyl magnesium chloride (MeMgCl).

5. The process according to claim 1, wherein the carbonate is dimethylcarbonate.

6. The process according to claim 1, wherein the compound of formula (III) is crystallized prior to its reaction to the compound of formula (I).

7. The process according to claim 6, wherein the crystallization of the compound of formula (III) is performed in isopropanol.

8. The process according to any one of claims 1-7, wherein the compound of formula (I) is Fesoterodine having the formula (Ia)

or a salt thereof.

9. The process according to claim 8 wherein the compound of formula (I) is the hydrogen fumarate salt of Fesoterodine.

10. The process according to any one of claim 1 or 9 wherein in step c) the carbonate is used in about 5-fold to 50-fold excess.

11. The process according to claim 10 wherein a solvent is used in step c).

12. The process according to claim 11, wherein the solvent is hexane.

13. The process according to claim 12, wherein in step c) the carbonate is dissolved in hexane and then distilled to reduce the water content to 0.01% or below and then the Grignard reagent is added.

14. The process according to claim 1, wherein the reaction step c) is followed by quenching the mixture with a suitable reagent.

15. The process according to claim 14 wherein the reagent is aqueous ammonium chloride.

16. The process according to claim 1, wherein the molar ratio of the Grignard initiator to Mg is between 1:2 and 2:1, and the molar ratio of the Grignard initiator to the compound of formula (II) is between about 1:1 and 2:1.

17. The process according to claim 1, wherein step a) is conducted by
  a1) dissolving the compound of formula (II) in a suitable solvent to form a solution, and
  a2) adding the solution to a mixture of the Grignard initiator and Mg in a suitable solvent.

18. The process according to claim 17, wherein the solvent in step a1) used for dissolving the compound of formula (II) is toluene.

19. The process according claim 17, wherein the solvent in step a2) is THF.

20. The process according to claim 17, wherein
  in step a1) the compound of formula (II) is dissolved in toluene,
  in step a2) the solution is added to a mixture of the Grignard initiator and Mg in THF and stirred until the completion of the reaction,
  before step c), the mixture as obtained in step a2) is maintained under stirring at a temperature below the temperature of the reaction of step a2),
  in step c) the mixture is added to an excess of carbonate in hexane, followed by quenching with aqueous $NH_4Cl$.

21. The process according to claim 1, wherein the reaction temperature of step a) is between 40 and 50° C.

22. The process according to claim 2, wherein the temperature of the Grignard reagent is reduced to between 20 and 25° C.

23. The process according to claim 1, wherein the reaction temperature of step c) is below 10° C.

24. The process according to claim 1, wherein in step c) the reaction mixture is stirred at an agitation speed of ≧90 rpm.

25. A process for the preparation of a pharmaceutical composition containing Fesoterodine hydrogen fumarate comprising the steps of
   (a) preparing Fesoterodine hydrogen fumarate by the process according to claim 9, and
   (b) formulating the thus obtained Fesoterodine hydrogen fumarate to obtain a pharmaceutical composition.

26. A process for the preparation of an intermediate in the production of 2-(3-diisopropylamino-1-phenylpropyl)-4-(hydroxymethylphenol) (Fesoterodine) comprising the step of reacting a carbonate selected from the group of di($C_1$-$C_6$ alkyl) carbonates and cyclic $C_2$-$C_6$ alkylene carbonates, with a Grignard reagent to obtain a compound of formula (III)

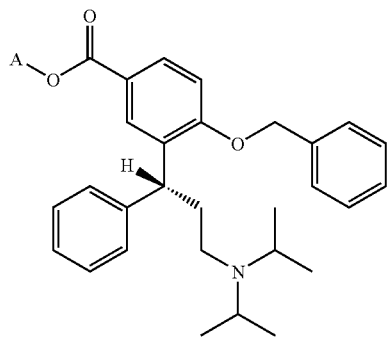

(III)

wherein A is a $C_1$-$C_6$ alkyl group, and wherein the Grignard reagent is formed by reacting a compound of formula (II)

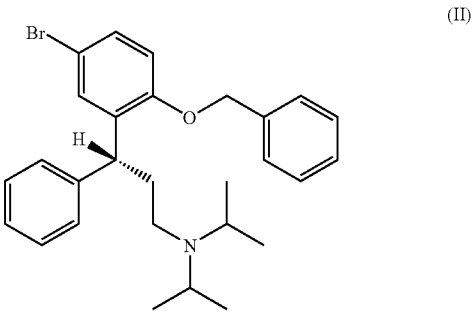

(II)

with a mixture of Mg and a Grignard initiator of the formula $R^1$—MgX, wherein $R^1$ represents $C_1$-$C_{12}$ alkyl, $C_2$-$C_6$ alkenyl, $C_2$-$C_6$ alkynyl, substituted or unsubstituted phenyl or phenyl($C_1$-$C_6$)alkyl, and wherein X is selected from bromide, chloride and iodide, in a solvent.

27. Method according to claim 26, wherein the Grignard initiator is MeMgCl, and the carbonate is dimethylcarbonate.

28. Method according to claim 26 comprising the crystallization of the compound of formula (III) in isopropanol.

* * * * *